United States Patent
Sharkey et al.

[11] Patent Number: 5,954,716
[45] Date of Patent: *Sep. 21, 1999

[54] METHOD FOR MODIFYING THE LENGTH OF A LIGAMENT

[75] Inventors: Hugh R. Sharkey, Woodside; Gary S. Fanton, Portola Valley, both of Calif.

[73] Assignee: Oratec Interventions, Inc, Menlo Park, Calif.

[*] Notice: This patent is subject to a terminal disclaimer.

[21] Appl. No.: 09/025,984

[22] Filed: Feb. 19, 1998

Related U.S. Application Data

[60] Provisional application No. 60/037,783, Feb. 19, 1997, abandoned.

[51] Int. Cl.$^6$ .................................................. A61B 17/38
[52] U.S. Cl. .................................................. 606/32
[58] Field of Search .................. 606/27, 28, 29, 606/30, 31, 32, 33, 34, 41, 73, 79, 80, 86, 92, 93

[56] References Cited

U.S. PATENT DOCUMENTS

| | | | |
|---|---|---|---|
| 2,090,923 | 8/1937 | Wappler | 128/303.15 |
| 3,178,728 | 4/1965 | Christensen | 3/1 |

(List continued on next page.)

FOREIGN PATENT DOCUMENTS

| | | | |
|---|---|---|---|
| 0 257 116 A1 | 3/1988 | European Pat. Off. | A61N 1/36 |
| 0 274 705 A1 | 7/1988 | European Pat. Off. | A61M 23/00 |

(List continued on next page.)

OTHER PUBLICATIONS

Auhll, Richard A., "The Use of the Resectoscope in Gynecology." Biomedical Business International, Oct. 11, 1990, pp. 91–93.

Christian, C. et al., "Allograft Anterior Cruciate Ligament Reconstruction with Patellar Tendon: An Endoscopic Technique", *Operative Techniques in Sports Medicine*, vol. 1, No. 1, Jan. 1993, pp. 50–57.

Houpt, J. et al., "Experimental Study of Temperature Distributions and Thermal Transport During Radiofrequency Current Therapy of the Intervertebral Disc", *Spine*, vol. 21, No. 15, (1996), pp. 1808–1813.

Troussier, B. et al., "Percutaneous Intradiscal Radio–Frequency Thermocoagulation: A Cadaveric Study", *Spine*, vol. 20, No. 15, (Aug. 1995), pp. 1713–1718.

Beadling, L., "Bi–Polar electrosurgical devices: Sculpting the future of arthroscopy", *Orthopedics today*, vol. 17, No. 1, Jan. 1997, 4 pages.

Ellman International Mfg., Inc., 1989, Catalog, pp. 1–15, 20.

Cosset, J.M., Resistive Radiofrequency (Low Frequency) Interstitial Heating (RF Technique), Interstitial Hyperthermia, Dec. 6, 1993, pp. 3–5, 37.

Attachment I: Competitive Literature on Generators with Bipolar Capabilities, IME Co., Ltd., pp. 60–86.

Attachment II: Competitive Literature on Bipolar Forceps and Footswitch Controls, IME Co., Ltd. pp. 87–104.

*Primary Examiner*—George Manuel
*Attorney, Agent, or Firm*—Wilson, Sonsini, Goodrich & Rosati

[57] ABSTRACT

A method for modifying a ligament connection between two bones by applying radio frequency energy to a portion of a ligament in a patient that functions to maintain two or more bones in a standard configuration in a species to which the patient belongs, but which are in a relationship to each other that is not medically acceptable in the patient, for a time sufficient to induce thermal shrinkage of the portion of the ligament. The method is particularly useful for skeletal-shift disorders by applying radio frequency energy to one ligament of a set of ligaments of a patient that function to align two or more bones in a standard configuration in a species to which the patient belongs but which are causing a skeletal shift in the patient because of an imbalance of ligament-induced forces in the patient for a time sufficient to induce thermal shrinkage of the portion of the ligament, thereby alleviating the skeletal shift. Patellar shift and curvature of the spine are two examples of such disorders.

12 Claims, 2 Drawing Sheets

U.S. PATENT DOCUMENTS

| | | | |
|---|---|---|---|
| 3,579,643 | 5/1971 | Morgan | 3/1 |
| 3,776,230 | 12/1973 | Neefe | 128/260 |
| 3,856,015 | 12/1974 | Iglesias | 128/303.15 |
| 3,867,728 | 2/1975 | Substad et al. | 3/1 |
| 3,879,767 | 4/1975 | Substad | 3/1 |
| 3,886,600 | 6/1975 | Kahn et al. | 3/1 |
| 3,938,198 | 2/1976 | Kahn et al. | 3/1.912 |
| 3,945,375 | 3/1976 | Banko | 128/6 |
| 3,987,499 | 10/1976 | Scharbach et al. | 3/1.91 |
| 3,992,725 | 11/1976 | Homsy | 3/1 |
| 4,043,342 | 8/1977 | Morrison, Jr. | 128/303.14 |
| 4,085,466 | 4/1978 | Goodfellow et al. | 3/1.91 |
| 4,129,470 | 12/1978 | Homsy | 156/155 |
| 4,134,406 | 1/1979 | Iglesias | 128/303.15 |
| 4,224,696 | 9/1980 | Murray et al. | 3/1.911 |
| 4,224,697 | 9/1980 | Murray et al. | 3/1.911 |
| 4,326,529 | 4/1982 | Doss et al. | 128/303.1 |
| 4,344,193 | 8/1982 | Kenny | 3/1.911 |
| 4,362,160 | 12/1982 | Hiltebrandt | 128/303.15 |
| 4,375,220 | 3/1983 | Matvias | 128/804 |
| 4,381,007 | 4/1983 | Doss | 128/303.1 |
| 4,397,314 | 8/1983 | Vaguine | 128/399 |
| 4,476,862 | 10/1984 | Pao | 128/303.17 |
| 4,483,338 | 11/1984 | Bloom et al. | 128/303.13 |
| 4,517,965 | 5/1985 | Ellison | 128/20 |
| 4,517,975 | 5/1985 | Garito et al. | 128/303.13 |
| 4,590,934 | 5/1986 | Malis et al. | 128/303.14 |
| 4,593,691 | 6/1986 | Lindstrom et al. | 128/303.14 |
| 4,597,379 | 7/1986 | Kihn et al. | 128/1 R |
| 4,601,705 | 7/1986 | McCoy | 604/94 |
| 4,651,734 | 3/1987 | Doss et al. | 128/303.14 |
| 4,811,733 | 3/1989 | Borsanyi et al. | 128/303.14 |
| 4,815,462 | 3/1989 | Clark | 128/305 |
| 4,838,859 | 6/1989 | Strassmann | 604/95 |
| 4,873,976 | 10/1989 | Schreiber | 128/334 R |
| 4,894,063 | 1/1990 | Nashef | 623/13 |
| 4,895,148 | 1/1990 | Bays et al. | 606/213 |
| 4,907,585 | 3/1990 | Schachar | 606/28 |
| 4,907,589 | 3/1990 | Cosman | 606/34 |
| 4,924,865 | 5/1990 | Bays et al. | 606/77 |
| 4,944,727 | 7/1990 | McCoy | 604/95 |
| 4,950,234 | 8/1990 | Fujioka et al. | 604/60 |
| 4,955,882 | 9/1990 | Hakky | 606/14 |
| 4,966,597 | 10/1990 | Cosman | 606/50 |
| 4,976,709 | 12/1990 | Sand | 606/5 |
| 4,976,715 | 12/1990 | Bays et al. | 606/77 |
| 4,998,933 | 3/1991 | Eggers et al. | 606/41 |
| 5,007,908 | 4/1991 | Rydell | 606/47 |
| 5,009,656 | 4/1991 | Reimels | 606/48 |
| 5,085,657 | 2/1992 | Ben-Simhon | 606/42 |
| 5,098,430 | 3/1992 | Fleenor | 606/42 |
| 5,100,402 | 3/1992 | Fan | 606/41 |
| 5,103,804 | 4/1992 | Abele et al. | 128/4 |
| 5,178,620 | 1/1993 | Eggers et al. | 606/41 |
| 5,186,181 | 2/1993 | Franconi et al. | 128/804 |
| 5,191,883 | 3/1993 | Lennox et al. | 128/401 |
| 5,192,267 | 3/1993 | Shapira et al. | 604/22 |
| 5,201,729 | 4/1993 | Hertzmann et al. | 606/2 |
| 5,201,730 | 4/1993 | Easley et al. | 606/4 |
| 5,213,097 | 5/1993 | Zeindler | 128/401 |
| 5,230,334 | 7/1993 | Klopotek | 128/399 |
| 5,242,439 | 9/1993 | Larsen et al. | 606/15 |
| 5,242,441 | 9/1993 | Avitall | 606/41 |
| 5,261,906 | 11/1993 | Pennino et al. | 606/46 |
| 5,267,994 | 12/1993 | Gentelia et al. | 606/15 |
| 5,275,151 | 1/1994 | Shockey et al. | 128/4 |
| 5,284,479 | 2/1994 | de Jong | 604/60 |
| 5,304,169 | 4/1994 | Sand | 606/5 |
| 5,308,311 | 5/1994 | Eggers et al. | 606/28 |
| 5,311,858 | 5/1994 | Adair | 128/4 |
| 5,320,115 | 6/1994 | Kenna | 128/898 |
| 5,323,778 | 6/1994 | Kandarpa et al. | 128/653.2 |
| 5,334,193 | 8/1994 | Nardella | 606/41 |
| 5,342,357 | 8/1994 | Nardella | 606/40 |
| 5,348,554 | 9/1994 | Imran et al. | 606/41 |
| 5,352,868 | 10/1994 | Denen et al. | 219/501 |
| 5,354,331 | 10/1994 | Schachar | 623/4 |
| 5,364,395 | 11/1994 | West, Jr. | 606/46 |
| 5,366,443 | 11/1994 | Eggers et al. | 604/114 |
| 5,366,490 | 11/1994 | Edwards et al. | 607/99 |
| 5,382,247 | 1/1995 | Cimino et al. | 606/33 |
| 5,397,304 | 3/1995 | Truckai | 604/95 |
| 5,401,272 | 3/1995 | Perkins | 606/15 |
| 5,415,633 | 5/1995 | Lazarus et al. | 604/95 |
| 5,423,806 | 6/1995 | Dale et al. | 606/15 |
| 5,433,739 | 7/1995 | Sluijter et al. | 607/99 |
| 5,437,661 | 8/1995 | Rieser | 606/15 |
| 5,437,662 | 8/1995 | Nardella | 606/40 |
| 5,451,223 | 9/1995 | Ben-Simhon | 606/42 |
| 5,458,596 | 10/1995 | Lax et al. | 606/31 |
| 5,465,737 | 11/1995 | Schachar | 128/898 |
| 5,484,403 | 1/1996 | Yoakum et al. | 604/59 |
| 5,484,432 | 1/1996 | Sand | 606/5 |
| 5,484,435 | 1/1996 | Fleenor et al. | 606/46 |
| 5,487,757 | 1/1996 | Truckai et al. | 607/122 |
| 5,500,012 | 3/1996 | Brucker et al. | 607/122 |
| 5,507,812 | 4/1996 | Moore | 623/13 |
| 5,514,130 | 5/1996 | Baker | 606/41 |
| 5,524,338 | 6/1996 | Martyniuk et al. | 29/825 |
| 5,542,920 | 8/1996 | Cherif Cheikh | 604/57 |
| 5,569,242 | 10/1996 | Lax et al. | 606/42 |
| 5,599,356 | 2/1997 | Edwards et al. | 606/41 |
| 5,630,839 | 5/1997 | Corbett, III et al. | 607/137 |
| 5,658,289 | 8/1997 | Boucher et al. | 606/73 |
| 5,681,282 | 10/1997 | Eggers et al. | 604/114 |
| 5,683,366 | 11/1997 | Eggers et al. | 604/114 |
| 5,688,270 | 11/1997 | Yates et al. | 606/51 |
| 5,697,909 | 12/1997 | Eggers et al. | 604/114 |
| 5,755,718 | 5/1998 | Sklar | 606/80 |

FOREIGN PATENT DOCUMENTS

| | | | |
|---|---|---|---|
| 0 479 482 A1 | 4/1992 | European Pat. Off. | A61B 17/39 |
| 0 521 595 A2 | 1/1993 | European Pat. Off. | A61M 25/01 |
| 0 558 297 A2 | 1/1993 | European Pat. Off. | A61M 25/00 |
| 0 542 412 A1 | 5/1993 | European Pat. Off. | A61B 17/39 |
| 0 566 450 A1 | 10/1993 | European Pat. Off. | A61N 5/02 |
| 0 572 131 A1 | 12/1993 | European Pat. Off. | A61B 17/39 |
| 0 682 910 A1 | 11/1995 | European Pat. Off. | A61B 1/00 |
| 0 729 730 A1 | 4/1996 | European Pat. Off. | A61B 17/32 |
| 0 479 482 B1 | 5/1996 | European Pat. Off. | A61B 17/39 |
| 0 737 487 A2 | 10/1996 | European Pat. Off. | A61M 25/01 |
| 0 783 903 A1 | 7/1997 | European Pat. Off. | A61N 5/04 |
| 1122634 | 9/1956 | France . | |
| 3511107A1 | 10/1986 | Germany | A61B 17/39 |
| 3632197A1 | 3/1988 | Germany | A61B 10/00 |
| 5-42166 | 5/1993 | Japan | A61B 17/39 |
| 637118 | 12/1978 | U.S.S.R. | A61B 17/18 |
| 1 340 451 | 12/1973 | United Kingdom | A61F 1/00 |
| 2 164 473 | 3/1986 | United Kingdom | A61B 17/36 |
| WO 85/02762 | 7/1985 | WIPO | A61B 17/36 |
| WO 92/10142 | 6/1992 | WIPO | A61B 17/36 |
| WO 93/01774 | 2/1993 | WIPO | A61F 7/12 |
| WO 93/20984 | 10/1993 | WIPO | B26D 1/11 |
| WO 95/01814 | 1/1995 | WIPO | A61N 5/02 |
| WO 95/13113 | 5/1995 | WIPO | A61N 5/02 |
| WO 95/18575 | 7/1995 | WIPO | A61B 17/39 |
| WO 95/20360 | 8/1995 | WIPO | A61B 17/39 |
| WO 95/30373 | 11/1995 | WIPO | A61B 17/00 |
| WO 96/34568 | 11/1996 | WIPO | A61B 17/36 |
| WO 96/39914 | 12/1996 | WIPO | A61B 1/00 |
| WO 97/06855 | 2/1997 | WIPO | A61N 1/40 |
| WO 98/07468 | 2/1998 | WIPO | A61N 1/40 |

METHOD FOR MODIFYING THE LENGTH OF A LIGAMENT

RELATIONSHIP TO COPENDING APPLICATIONS

This application is a continuation-in-part of U.S. Ser. No. 60/037,783 filed Feb. 19, 1997, now abandoned.

BACKGROUND OF INVENTION

1. Technical Field

This invention is directed to the field of surgery and is specifically directed to use of heat, especially that resulting from the application of radio frequency energy, to modify the length of ligaments.

2. Background

Instability of joints between bones has long been recognized as a significant cause of disability and functional limitation in patients. For example, diarthrodial joints of the musculoskeletal system have varying degrees of intrinsic stability based on joint geometry and ligament and soft tissue investment. Diarthrodial joints are comprised of the articulation of the ends of bones and their covering of hyaline cartilage surrounded by a soft tissue joint capsule that maintains the constant contact of the cartilage surfaces. This joint capsule also maintains, within the joint, the synovial fluid that provides nutrition and lubrication of the joint surfaces. Ligaments are soft tissue condensations in or around the joint capsule that reinforce and hold the joint together while also controlling and restricting various movements of the joints. Ligaments, joint capsule, and connective tissue are largely comprised of collagen.

When a joint between two or more bones becomes unstable, either through disease or traumatic injury, its soft tissue or bony structures allow for excessive motion of the joint surfaces relative to each other and in directions not normally permitted by the ligaments or capsule. Sometimes there is simply a malaligmnent problem, as occurs with various unnatural positions of vertebrae in the spin. When one surface of a joint slides out of position relative to the other surface, but some contact remains, subluxation occurs. When one surface of the joint completely disengages and loses contact with the opposing surface, a dislocation occurs. Typically, the more motion a joint normally demonstrates, the more inherently loose is the soft tissue surrounding the joint. This makes some joints more prone to instability than others. The shoulder, glenohumeral joint, for example, has the greatest range of motion of all peripheral joints. It has long been recognized as having the highest subluxation and dislocation rate because of its inherent laxity relative to more constrained "ball and socket" joints such as the hip.

Patent applications from the laboratory of the inventors have previously addressed some issues relating to joint instability. See, for example, U.S. patent application Ser. Nos. 08/637,095 and 08/714,987 (these applications also provide a thorough explanation of temperature control and energy supply systems that can be used with the present invention). Instability of the shoulder can occur congenitally, developmentally, or traumatically and often becomes recurrent, necessitating surgical repair. In fact, subluxations and dislocations are a common occurrence and cause for a large number of orthopedic procedures each year. Symptoms include pain, instability, weakness and limitation of function. If the instability is severe and recurrent, functional incapacity and arthritis may result. Surgical attempts are directed toward tightening the soft tissue restraints that have become pathologically loose. These procedures are typically performed through open surgical approaches that often require hospitalization and prolonged rehabilitation programs.

More recently, endoscopic endoscope (arthroscopic) techniques for achieving these same goals have been explored with variable success. Endoscopic techniques have the advantage of being performed through smaller incisions, and therefor are usually less painful. Such techniques are performed on an outpatient basis, associated with less blood loss and lower risk of infection and have a more cosmetically acceptable scar. Recovery is often faster postoperatively than using open techniques. However, it is often more technically demanding to advance and tighten capsule or ligamentous tissue arthroscopically because of the difficult access to pathologically loose tissue, and because it is very hard to determine how much tightening or advancement of the lax tissue is clinically necessary. In addition, fixation of advanced or tightened soft tissue is more difficult arthroscopically than through open surgical methods.

Collagen connective tissue is ubiquitous in the human body and demonstrates several unique characteristics not found in other tissues. It provides the cohesiveness of the musculoskeletal system, the structural integrity of the viscera as well as the elasticity of integument. There are basically five types of collagen molecules, with Type I being most common in bone, tendon, skin and other connective tissues, and Type III is common in muscular and elastic tissues.

Intermolecular cross-links provide collagen connective tissue with unique physical properties of high tensile strength and substantial elasticity. A previously recognized property of collagen is hydrothermal shrinkage of collagen fibers when elevated in temperature. This unique molecular response to temperature elevation is the result of rupture of the collagen stabilizing cross-links and immediate contraction of the collagen fibers to about one-third of their original lineal distention. Additionally, the caliber of the individual fibers increases greatly, over four-fold, without changing the structural integrity of the connective tissue.

There has been discussion in the existing literature regarding alteration of collagen connective tissue in different parts of the body. One known technique for effective use of this knowledge of the properties of collagen is through the use of infrared laser energy to effect tissue heating. The importance in controlling the localization, timing and intensity of laser energy delivery is recognized as paramount in providing the desired soft tissue shrinkage without excessively damaging the surrounding non-target tissues.

Shrinkage of collagen tissue is important in many applications. One application is the shoulder capsule. The capsule of the shoulder consists of a synovial lining and three well-defined layers of collagen. The fibers of the inner and outer layers extend in a coronal access from the glenoid to the humerus. The middle layer of the collagen extends in a sagittal direction, crossing the fibers of the other two layers. The relative thickness and degree of intermingling of collagen fibers of the three layers vary with different portions of the capsule. The ligamentous components of the capsule are represented by abrupt thickening of the inner layer with a significant increase in well-organized coarse collagen bundles in the coronal plane.

The capsule functions as a hammock-like sling to support the humeral head. In pathologic states of recurrent traumatic or developmental instability this capsule or pouch becomes attenuated, and the capsule capacity increases secondary to capsule redundance. In cases of congenital or developmental multidirectional laxity, an altered ratio of Type I to Type III collagen fibers may be noted. In these shoulder capsules, a higher ratio of more elastic Type III collagen has been described. Shrinkage of capsule collagen to improve shoulder function was previously developed in the laboratory of the inventors.

Additionally, there are a number of skeletal disorders associated with malalignment of adjacent bones that are caused by either incorrect tension available from a ligament or from a group of separate ligaments, resulting either from disease or traumatic injury. Prior investigations into methods of tightening the capsule of the shoulder joint, an earlier focus of research in the laboratory of the present inventors, has shown a need for more focused research and improvements in methods of treating disorders associated with medically incorrect (under disease or post-traumatic conditions) ligament tension. The need for such further developments has led to the present invention.

SUMMARY OF THE INVENTION

Accordingly, it is an object of the present invention to provide a technique for straightening malaligned bones.

It is another object of the present invention to provide a method for adjusting the length of a ligament graft.

It is still another object of the present invention to provide a method of adjusting tension in a natural ligament.

It is a further object of the present invention to provide treatments for patellar shift and spinal column malalignment.

These and other objects of the invention have been accomplished by providing a method for modifying a ligament connection between two bones by heat energy to a portion of a ligament in a patient that functions to maintain two or more bones in a standard configuration in a species to which the patient belongs, but which are in a relationship to each other that is not medically acceptable in the patient, for a time sufficient to induce thermal shrinkage of the portion of the ligament.

The method can be applied to skeletal-shift disorders by applying heat energy to one ligament of a set of ligaments of a patient that function to align two or more bones in a standard configuration in a species to which the patient belongs, but which are causing a skeletal shift in the patient because of an imbalance of ligament-induced forces in the patient, for a time sufficient to induce thermal shrinkage of the portion of the ligament, thereby alleviating the skeletal shift. Patellar shift and curvature of the spine are two examples of such disorders.

Radio frequency (RF) energy is particularly preferred as a heat source, although other energy sources can be used.

BRIEF DESCRIPTION OF THE DRAWINGS

The invention now being generally described, the same will be better understood by reference to the drawings that form part of this specification, wherein.

DETAILED DESCRIPTION OF PREFERRED EMBODIMENTS.

The present invention is directed to a method for tightening a ligament connection between two bones by applying heat, preferably but not necessarily resulting from application of radio frequency energy, to a portion of a ligament in a patient that functions to maintain two or more bones in a standard configuration in a species to which the patient belongs, but which are in a relationship to each other that is not medically acceptable in the patient, for a time sufficient to induce thermal shrinkage of the portion of the ligament. The initial heating of the collagen in the ligament causes a contraction of the ligament (if it is not subject to stretching forces), but the ligament is weaker than it was prior to heat treatment and cam be stretched under tension to a length greater than it had previously. On the other hand, maintaining tension in the ligament less than that necessary to stretch the portion of the ligament subjected to thermal shrinkage until the portion has regained sufficient strength to maintain the bones in the standard configuration results in shortening of the ligament. Many different disorders of ligaments and injuries can be treated by shortening one or more ligaments using the method of the invention.

Examples of medical conditions that can be treated include cases in which the ligament being treated is a surgical graft ligament and the thermal shrinkage is applied to adjusting the length of the ligament after attachment of the graft ligament to the bones. In other cases, a natural ligament is being shortened as in straightening curvature of the spine or modifying ligament tensions to correct patellar shift.

The invention is particularly useful when used in arthroscopic applications, since it is often difficult in such situations to accurately incise or trim ligaments, and in the adjustment of graft length, since initial creation of a graft having the exact length necessary to achieve a desired function is difficult. In most such cases, an insulated probe having an electrode in a distal portion thereof is introduced into a body cavity adjacent the ligament being treated and RF energy sufficient to shrink collagen is applied to the ligament through the electrode. Certain advantages are present when energy is applied to the ligament by two electrodes positioned on opposite sides of the ligament rather than by simply heating the tendon by use of an electrode applied to one side of the ligament, whether the electrode is monopolar or bipolar. Such probes are described in a patent application filed on the same day as the present specification from the laboratory of the present inventors (Attorney Docket No. ORAT-011/00US entitled "Method and Apparatus for the Treatment of Strabismus") and directed specifically to the treatment of strabismus, a disorder that can be alleviated by the adjustment of the length of extraocular tendons. Probes of a similar shape but sized to engage a ligament, with different probes being prepared and sized for different ligaments (depending on the intended end use), can be used in the practice of the present invention.

Situations involving desired shortening of the ligament require that the tension on the ligament be maintained below that necessary to stretch the portion of the ligament until sufficient time has elapsed to allow the ligament to regain its strength. The desired time can best be judged empirically by a physician familiar with the stresses likely to be placed on the ligament by the patient. For example, the stress likely to be encountered by the anterior cruciate ligament of a knee of a professional football player will be greater than the stress likely to be encountered by an office worker, which may require different recovery regimens for the two patients. Different times of stress relief for different patients is therefor required, as may different techniques (for example, required by the weight of the patient or the location of the ligament). In some cases tension can be relieved by tension-relieving sutures in the ligament itself, which can optionally be selected to dissolve in the body so that further surgery is avoided. In other cases, it will be appropriate to maintain the tension below that necessary to stretch the portion of the ligament by maintaining the bones in a low-tension substantially fixed position, such as by protecting the treated joint of a patient with a cast, sling, or crutches or similar device.

One regimen would be to protect the joint from stress for 10 days, after which the surgeon would evaluate the range and ease of motion. If the joint were too loose, it would be protected longer (perhaps another 10 days—up to 6 weeks total). If the joint were too tight, stretching rehabilitation aimed at obtaining normal function would be undertaken. Physician monitoring of the patient, with rest or stress relief once the proper length is attained, is the best way to improve the proper lengthening of a ligament, since each patient will provide a different activity, body weight, and temperament to be taken into consideration in the prescription of appropriate stress and later rest.

The method of the invention can be combined with other medical techniques designed to alleviate the condition being treated, such as by releasing tension on the ligament being treated by a surgical incision in a ligament not being treated, as well as other techniques known for adjusting ligament placement or tension.

The method of the invention is particularly useful for treating ligament-induced skeletal shift, such as patellar shift or curvature of the spine, that involve two or more ligaments attached to different parts of the same bones of a bone joint, such as the knee or spinal column. In such cases radio frequency energy (or another energy source) is applied to a portion of one ligament of a set of ligaments of a patient. The ligament set functions to align two or more bones in a standard configuration in a species to which the patient belongs, but are causing a skeletal shift in the patient because of an imbalance of ligament-induced forces in the patient resulting from disease or injury. Although most patients being treated by this method are expected to be human, veterinary use is also possible. Energy is applied for a time sufficient to induce thermal shrinkage of the portion of the ligament, thereby alleviating the skeletal shift. "Shrinkage" here (and elsewhere in this specification) refers to the initial collagen shrinking process and the initial resulting shortening (unless otherwise is clear from the context of the word), since final length of the ligament is the result of the initial shrinkage combined with growth of collagen into the affected area, and tension or lack of tension on the ligament. Preferred treatments are for patellar shift, where the ligament being treated is a medial ligament being shortened, and malalignment of the spinal column, where the ligament is one of a pair of ligaments on opposite sides of the spinal column.

Turning now to techniques and apparatuses that can be used in the present invention, reference is made to the numerous patents and applications that exist involving the shrinkage of collagen in vivo, including the following from the laboratory of the present inventors: U.S. Pat. No. 5,458,596; U.S. Pat. No. 5,569,242; and U.S. applications Ser. Nos. 08/637,095, 08/714,987, 08/320,304, 08/547,510, 08/390,873, 08/616,752, 08/696,051, 08/700,195, 60/029,600, 60/029,602, 60/029,734, and 60/029,735. Other patents of interest include U.S. Pat. Nos. 4,976,709; 4,326,529; and 4,381,007. All of these patents and applications describe apparatuses, power supplies, surgical procedures, or other components of systems that can be adapted to the practice of the present invention when following the guidance provided in the current specification. As an example of some of the components that can be used in the practice of the present invention, the following description is given of previously developed components from the laboratory of the inventors that can be adapted to the practice of the present invention.

Figure 1:
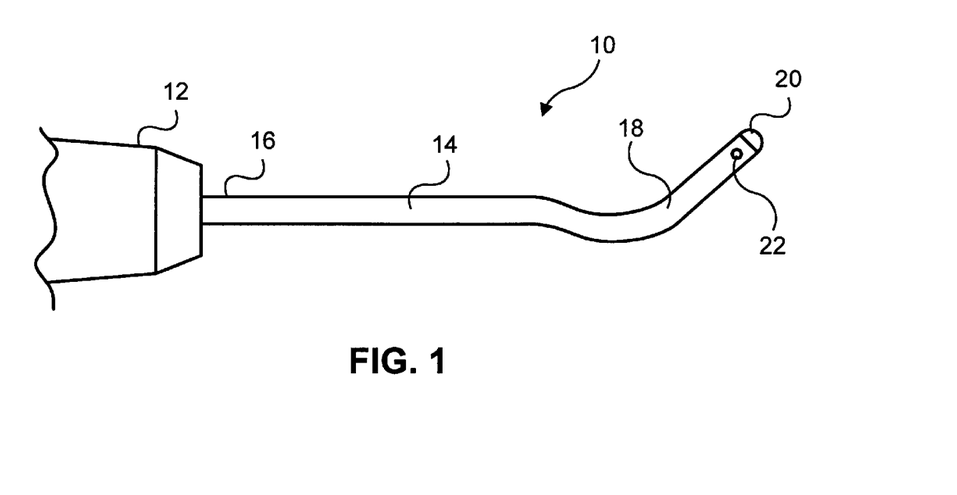
FIG. 1 is a perspective plan view of an embodiment of the present invention illustrating an apparatus for contracting collagen containing ligament.

Referring now to FIG. 1, an apparatus for shrinking collagen containing ligament to a desired level is generally denoted as 10. Apparatus 10 includes a handpiece 12 that is preferably made of a thermal insulating material. Types of such insulating materials are well known to those skilled in the art. An energy delivery device (e.g., RF electrode) 14 is coupled to handle 12 at a proximal end 16 of energy delivery device 14 and may be permanently or impermanently attached thereto. A distal end 18 of energy delivery device 14 includes a distal portion 20 which may have a geometry that delivers a controlled amount of energy to tissues in order to achieve a desired level of contraction of collagen fibers in a collagen containing ligament. Located at distal portion 20 is one or more sensors 22 which provide a signal whose magnitude is representative of the amount of thermal energy sensed.

Figure 2:
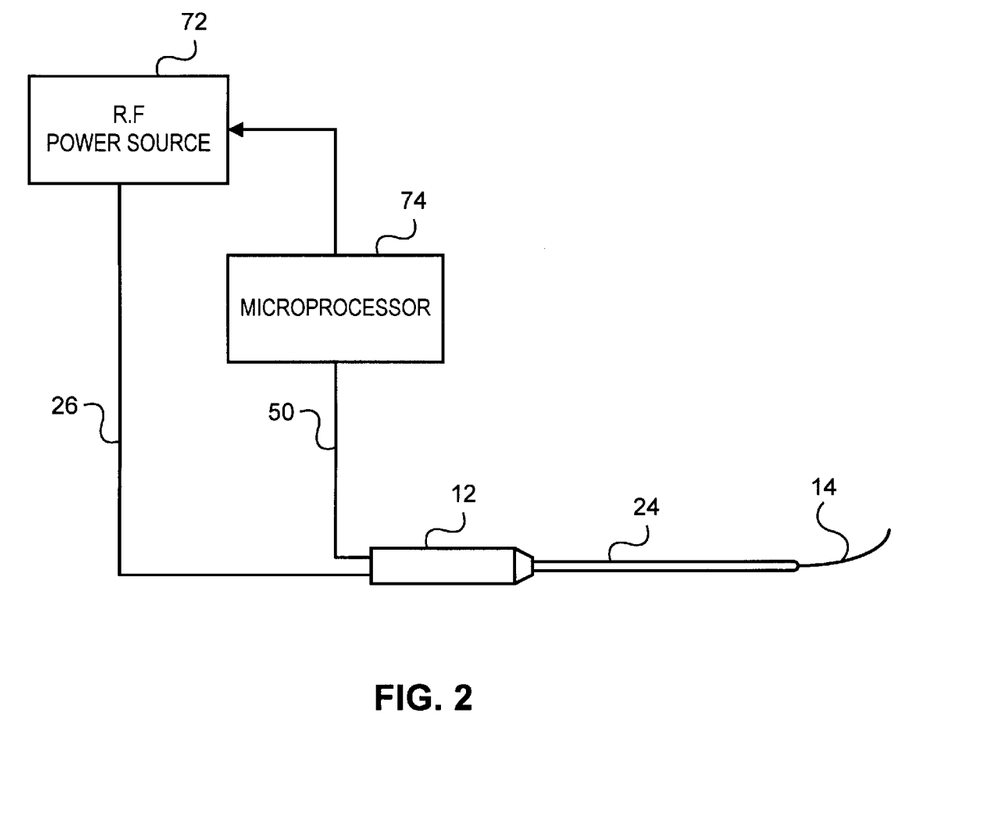
FIG. 2 is a perspective plan view of an embodiment of the present invention illustrating an apparatus coupled to an energy source for contracting collagen containing ligament.

As shown in FIG. 2, energy is supplied from an energy source 72 through a cable 26 to energy delivery device 14 at the end of probe neck 24 attached to handle 12. Since several types of energy can cause an elevation in the temperature of a collagen containing ligament 28, energy source 72 can include but is not limited to RF, microwave, ultrasonic, coherent and incoherent light, thermal transfer, and resistance heating. Return cable 50 from a sensor (not shown) provides feedback control through signal processing by microprocessor 74.

Figure 3:
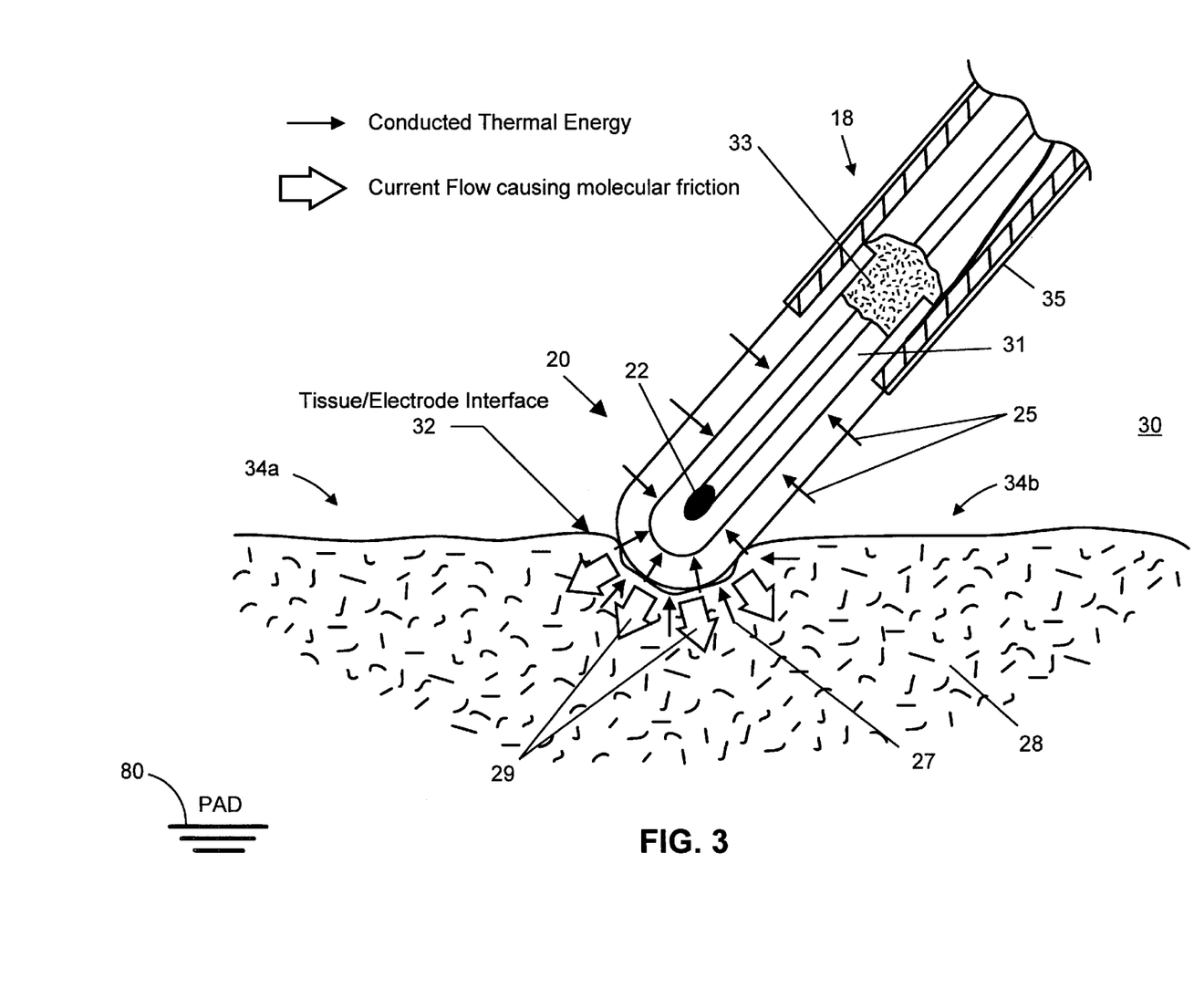
FIG. 3 illustrates the positioning of a distal end of an energy delivery device while delivering energy to a selected tissue site and a portion of an adjacent fluid medium and the measurement of a composite temperature.

As illustrated in FIG. 3, distal portion 20 of the probe contains the electrode that is positioned during operation adjacent to a collagen containing ligament 28 which is at least partially adjacent to a fluid medium 30. Appropriate collagen containing ligaments 28 for the purpose of the present invention includes ligaments. Distal portion 20 is preferably in contact with collagen containing ligament 28. Fluid medium (usually sterile saline) 30 may be flowing as would result from irrigating collagen containing ligament 28, or it may be substantially less dynamic or non-moving. During the procedure, the fluid medium 30 also contains pieces of bone, ligament blood and other tissue. Energy is delivered from distal portion 20 to a selected site 32 of the collagen containing ligament 28. Selected site 32 receives at least a portion of the delivered energy. Once the energy is delivered, it becomes thermal energy, causing the thermal energy content and the temperature of selected site 32 to increase. As the thermal energy content of selected site 32 is increased, thermal energy is conducted to the collagen fibers in and around selected site 32. Collagen fibers exposed to sufficient thermal energy lose their triple helix shape. Since the triple helix shape of collagen fibers is the longest shape for collagen fibers, fibers which lose their triple helix shape will contract. Thus, the delivery of energy to selected site 32 causes the temperature and the thermal energy content of selected site 32 to increase and effects collagen fiber contractions. The collagen fiber contraction results in a contraction of collagen containing ligament 28.

Energy delivery device 14 is configured to deliver a desired level of energy to selected site 32. Sensor 22 (an internal sensor in this embodiment) provides a signal indicative of a composite temperature of at least selected site 32 and at least a portion of adjacent fluid medium 30 to a feedback control unit. The signal is received by a feedback control system which adjusts the level of energy supplied to energy delivery device 14 and delivered to selected site 32 based on the signal received from sensor 22.

Throughout the treatment, it is often desirable to effect contractions in a selected area 34 which is larger than a selected site 32, such as they are extending from 34a to 34b in FIG. 3. Further, it may be desirable to elevate the temperature of the selected site 32 or selected area 34 to a desired average temperature for a specified period of time. There are several methods available for achieving these results. For instance, one embodiment is to "paint" distal portion 20 across selected area 34 by continually moving distal portion 20 over the surface of the selected area 34 so that the entire selected area 34 is covered. Selected area 34 can then be brought to the desired temperature and retained at that temperature by continually moving distal portion 20 over selected area 34. In another embodiment, distal portion 20 is left at selected site 32 until the desired temperature is obtained for the desired time. Distal portion 20 is then moved to another selected site 32 for a desired time. This pattern is repeated until the entire selected area 34 is covered. A combination of these techniques may also be used.

The composite temperature read by a temperature sensor at the site of heat treatment is a combination of at least two different temperatures in some ratio. One temperature 25 is from at least a portion of adjacent fluid medium 30 and another temperature 27 of at least a portion of selected tissue site 32. This ratio is a function of different parameters including but not limited to the size, shape, dimensions and geometry of a thermal energy delivery surface of energy delivery device 72, the portion of the thermal energy delivery surface that is in contact with adjacent fluid medium 30 and selected tissue site 32, and the location of sensor 22 in relationship to the thermal energy delivery surface. Current flow 29, which creates molecular friction, and conducted thermal energy are greater in selected tissue site 32 because the probe is pressed into the site and the dipole is on the opposite side of this side and the constant entry of room temperature saline into the operating field maintains the fluid temperature at 20° C. than in adjacent fluid medium 30 due to the higher resistance of the tissue. At the thermal energy-delivery-device/fluid-medium interface there is less resistance than at the tissue interface and a hydrodynamic force, which contribute to a lower reflected temperature. At the tissue interface there is a static conductive situation with a higher resistance producing higher reflective temperature at the interface.

In the embodiment of distal portion 20 illustrated in FIG. 3, distal portion 20 includes sensor 22 positioned in an interior of distal portion 20. A thermally conductive material 31 at least partially surrounds sensor 22 and a potting compound 33 is included. Distal end 18 is made of stainless steel, and a nylon coating 35 insulates that part of the exterior surface of distal portion 20 that does not function as an electrode.

The apparatus 10 in the embodiment shown in FIGS. 1–3, delivers monopolar RF power through the distal portion 20 to ground pad 80 [See FIG. 3]. As will be obvious to those skilled in the art, the apparatus can be configured to deliver RF energy in a bipolar arrangement. The electrode or other device 14 used to deliver energy can be made of a number of different materials including but not limited to stainless steel, platinum, other noble metals, and the like. The electrode can also be made of a memory metal, such as nickel titanium, commercially available from Raychem Corporation, Menlo Park, Calif. The electrode can also be of composite construction whereby different sections are constructed from different materials. Electrodes formed to deliver energy directionally, as described in an application from the laboratory of the present inventors filed the same day as the present application (attorney docket No. ORAT-013/00US and entitled "Electrode for Electrosurgical Ablation of Tissue") can also be used in the practice of the present invention.

Feedback control systems can be used to obtain the desired degree of contraction by maintaining selected site 32 at a desired temperature for a desired time. It has been shown that temperatures of 45 to 90° C. can cause collagen fiber contractions. It has also been shown that the degree of collagen fiber contraction is controlled by how long the temperature is elevated as well as how high it is elevated. Thus, the same degree of contraction can be obtained by exposing selected site 32 to a high temperature for a short period of time or by exposing selected site 32 to a lower temperature for a longer period of time. A preferred range for desired temperatures is about 45 to 75° C.; still a more preferred range is 45 to 65° C.. Before treatment, the surgeon evaluates the characteristics of the selected site 32 to determine what degree of contraction is necessary and also whether it is appropriate to treat the selected site 32 with a high temperature for a low period of time or lower temperature for a long period of time. The surgeon then controls the temperature either manually or through a system with feedback and automatic control.

Sensor 22 can consist of, but is not limited to, a thermocouple, a thermistor, or phosphor-coated optical fibers. The sensor 22 can be in an interior of the distal portion 20 or on the surface of the distal portion 20 and can further be a single sensor 22 or several sensors. It can also be a band or patch instead of a sensor 22 which senses only discrete points.

Sensor 22 provides a signal whose magnitude is representative of the thermal energy content of the surfaces and mediums in physical contact with the surface of the sensor 22. Thus, if several surfaces or mediums are in physical contact with sensor 22, the magnitude of the signal provided by sensor 22 will be representative of a composite of the thermal energy contents of those surfaces and/or mediums. Further, the effective surface of sensor 22 can be increased by wholly enclosing sensor 22 in a medium which easily conducts thermal energy. In this embodiment, thermal energy will be conducted from the surface of the thermally conductive medium to the sensor 22. The magnitude of the signal will represent a composite of the thermal energy contents of any surfaces and mediums in physical contact with the surface of the thermally conductive medium.

Apparatus 10, comprising handpiece 12 and distal portion 20 with an electrode or other energy delivery device, is adapted to be introduced through an operating cannula for percutaneous applications. It will be appreciated that apparatus 10 may be used in non-percutaneous applications and that an operating cannula is not necessary in the broad application of the invention.

Distal portion 20 of a probe generally includes an insulating layer 35 which is substantially impenetrable to the energy delivered to collagen containing ligament 28. Specifically, in the case of an RF electrode, electrical insulation can be used. Insulation 35 can be formed on the probe such that a minimum of energy is delivered to tissue, organs or other bodies which the surgeon does not wish to treat. For example, when an electrode is introduced into a tight area, and only one surface of the tight area is to be treated, it is desirable to avoid delivering energy outside of that surface. The inclusion of insulating layer 35 accomplishes this result. Suitable insulation materials include but are not limited to nylon, teflon, polyamide, epoxy varnish, PVC and the like.

The area of the energy delivery device (e.g., electrode) that serves as a conductive surface can be adjusted by the inclusion of an insulating sleeve that is positioned around the energy delivery device. The sleeve may be advanced and retracted along the surface of the energy delivery device in order to increase or decrease the surface area of conductive surface that is directed to collagen containing ligament 28. The sleeve can be made of a variety of materials including but not limited to nylon, polyamides, other thermoplastics and the like. The amount of available conductive surface available to deliver thermal energy can be achieved with devices other than a sleeve, including but not limited to printed circuitry with multiple circuits that can be individually activated, and the like.

The surgeon determines which collagen containing ligament 28 requires contraction and how much shrinkage should occur. The surgeon then selects an area of the collagen containing ligament 28 for shrinkage. The surgeon can find the selected area 34 by using arthroscopic viewing or using the apparatus 10 including a viewing scope. Once the surgeon places the energy delivery device next to the selected site 32, the surgeon soon begins delivery of energy.

Current and voltage are used to calculate impedance. An operator-set level of power and/or temperature may be determined, and this level can be maintained manually or automatically if desired. The amount of RF energy delivered controls the amount of power. Feedback can be the measurement of impedance or temperature and occurs either at controller or at RF source if it incorporates a controller. Impedance measurement can be achieved by supplying a small amount of non-therapeutic RF energy. Voltage and current are then measured to confirm electrical contact.

Circuitry, software and feedback to a controller result in full process control and are used to change (i) power (modulate)—including RF, incoherent light, microwave, ultrasound and the like, (ii) the duty cycle (on-off and wattage), (iii) monopolar or bipolar energy delivery, (iv) fluid (electrolytic solution delivery, flow rate and pressure and (v) determine when ablation is completed through time, temperature and/or impedance.

A monopolar electrode is a part of a circuit that includes the RF signal generator, connecting cables, probe tip for insertion into a joint space (or other fluid-filled bodily cavity), the patient's body, an indifferent or grounding electrode attached to the patient's body at a remote site and the return cable that connects the grounding electrode to the RF generator completing the circuit. Because such an RF electrode is a relatively good conductor, the electrode itself does not heat up. The tissues that the electrode comes in contact with, heat up in response to current passing from the electrode through the tissues. The tissue heats up because it is a relatively poor conductor as compared to the rest of the circuit. It is when the tissues heat up as a result of molecular friction, that heat is then conducted back to the electrode itself. At that point, a thermocouple (TC) within the electrode tip, senses the increase in temperature and supplies that information to the RF generator so that the feedback mechanism can attenuate the energy delivered in order to attain temperature control. It is this feature (electrode does not heat) that makes RF advantageous over other forms of heating because the electrode cools immediately after use.

A monopolar electrode has multiple surfaces which may be in contact with tissue at only a small percentage of the surface of the electrode. The rest of the electrode is exposed to the fluid-filled medium (typically normal saline) of the arthroscopically instrumented joint space. This fluid is most often not heated and may even be much colder than the nodal body temperature (typically between 18° and 25° C.). Therefore, the temperatures the electrode is exposed to may be 25° C. over 70% of the electrode surface, and 65° C. at the surface of the electrode that is in contact with the target tissues.

A thermocouple embedded within a solid electrode would therefore read a composite temperature, for simplicity's sake, 70%—25° C. and 30%—65° C., whereas the temperature that is important to monitor is the 30%—65° C. alone. Some electrode configurations have been investigated that minimized the amount of exposure to the cold fluid medium. However, it was found that it is desirable to have an electrode that the operator can use on all surfaces to include the distal cross-sectional tip and the circumferential lateral aspects of the electrode side walls. Therefore, the electrode needs to be able to sense the highest temperatures at the tissue/electrode interface with minimal influence from the colder fluid medium.

This is accomplished by providing a hollow electrode, within which the thermocouple is located. This hollow compartment is filled with a heat sink paste and is potted (sealed) at the distal end to contain the heat sink paste within this compartment. It is this heat sink paste that conducts the elevated temperature within the confines of the hollow compartment that provides for the transmission of conducted heat from the hotter electrode zones. Since thermal energy is a relative, dynamic state, the higher temperatures of the tissue-interface electrode zones are preferentially transmitted within the heat sink compartment, improving the sensing of the target temperature.

In addition to monopolar electrodes, bipolar electrodes can also be used in the practice of the invention. Such electrodes provide both electrodes necessary to complete the circuit on the same handpiece, usually at the tip of the probe. No further electrode for completion of the circuit is required.

In some uses of electrosurgical devices, the power electrode is moved soon after the target temperature is attained since coagulation of the tissues is accomplished fairly quickly. As the electrode is moved it encounters cooled or nonheated tissue. That non-heated tissue initially cools the electrode until molecular friction again heats the tissue. The heating of the new tissue, (and in turn heating the electrode) becomes a continuous process as the electrode is moved and a new electrode/tissues interface is established at each point along the path of the electrode's movement.

As may not be apparent from the discussion so far, the fluid in the joint space is in constant motion. Often these irrigating fluids flow through the joint by means of a series of in-flow and out-flow cannulas connected to a pump. The effect is that there is a convection of heat away from the electrode surface which is exposed to the fluid medium and not in contact with the tissue.

Applications from the laboratory of the inventors have previously described other methods of capturing target temperatures within a dynamic, coot fluid environment. They include the concave electrodes ("red blood cell shaped") with fenestrated concavities containing a thermocouple so that when the rim of the electrode is in contact with the tissues to be heated, a small amount of fluid is trapped within the concavity which heats in response to the tissues heating. This thermal energy then is sensed by the TC which may not be in contact with the target tissue, by the conduction of energy through the fluid. These can be both monopolar or bipolar; two sided or one sided.

EXAMPLE

The present invention can be illustrated by consideration of methods for treatment of dislocation of the kneecap (patellar shift). Release of the patella can be accomplished with the use of thermal energy applied to the patellar ligaments to shorten or lengthen the side ligaments. For this operation to be performed arthroscopically, the knee joint is distended with a clear fluid, usually physiological saline. Initial distention can be done using a large syringe to inject saline into the joint space. Distention forces the bones of the joint apart, creating room to introduce instrumentation without damaging the cartilage.

Once the instrumentation has been inserted into the joint space, irrigation tubing and cannulas are positioned and hooked up to provide continual fluid exchange during the procedure. The most common systems are gravity flow or the use of an arthroscopic irrigation pump. Hanging bags of irrigation fluid on an IV pole raises them 3–4 feet above the operative site. This elevation creates enough pressure to distend and irrigate the joint. The fluid enters the joint through the sheath of the arthroscope and exits through a cannula placed in the superior lateral portal, or the reverse, through the cannula and out through the scope sheath. The exact setup is a matter of physician preference. The key to the proper function of any system is that the inflow volume must be equal to or slightly larger than the outflow volume. This restriction in the outflow creates the internal pressure that distends the joint.

With an arthroscopic irrigation pump, the bags do not need to be raised on an IV pole. The factors controlling distention of the joint are controlled automatically by the pump. The pump monitors the fluid pressure in the joint space using a pressure-sensing cannula and automatically increases or decreases fluid flow as needed to provide optimum viewing. As with the gravity flow system, fluid enters the joint cavity through the scope sheath or the cannula in the superior lateral portal.

Such an arthroscopic procedure requires the creation of two to five portals (entryways) into the joint capsule. To create a portal, the surgeon usually begins by making a small stab wound with a scalpel (e.g., No. 11 blade) at the desired site of the portal. Next, the wound is enlarged and extended with a trocar encased in a sleeve (cannula) through muscle tissue to the synovial membrane. The trocar is removed, leaving the cannula in place. Then the surgeon uses a blunt obturator (to avoid damage to menisci and articular cartilage) to puncture through the synovium into the joint cavity.

The obturator is removed and the cannula left in place. The cannula can be used to insert an arthroscope or for the inflow and outflow of irrigation fluid. If the surgeon elects to insert instruments percutaneously, the sleeve is removed.

For patellar release, the surgeon frequently will use three portals, one for the arthroscope, one for the instrument, and one for the drain. Additional portals may be created for the surgeon to access other areas of the knee (i.e., to tighten the medial retinaculum) during the procedure. Frequently, a superolateral (above and to the side of the patella) approach is used for the irrigation cannula. For the arthroscope and electrosurgical probe, anteromedial and anterolateral approaches often are chosen, because they are relatively safe (minimal potential tissue damage) and most surgeons have more experience with them.

Using the surgical setup as described, RF energy is applied to the lateral or medial ligament to adjust the length of the ligaments (and thus tension con and positioning of the patella). Since most cases of dislocation of the patella involve lateral movement of the patella (to the outside of the knee), ligaments on the medial side of the patella are shortened, while lateral ligaments are lengthened (if appropriate for the particular surgical operation being performed). In a typical operation, RF energy is applied to the medial ligament to shorten that side of the attachment without lengthening the lateral ligament (to avoid loosening the patellar placement). The degree of shortening should be determined by the physician depending on the condition of the individual being treated and the specific condition of that individual's dislocation. Depending on the stress to which the knee will likely be subjected, rest or immobilization can be prescribed for a time sufficient to allow new collagen to penetrate and strengthen the shrunken region of the ligament. Reduction of tension on the treated ligament for about 6 weeks is sufficient for many cases.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for modifying a ligament connection between two bones, comprising:
   (1) applying radio frequency energy to a portion of a ligament in a patient that functions to maintain two or more bones in a standard configuration in a species to which said patient belongs but which bones are in a relationship to each other that is not medically acceptable in said patient for a time sufficient to induce thermal shrinkage of said portion of said ligament, and
   (2) maintaining tension in said ligament less than that necessary to stretch said portion of said ligament subjected to thermal shrinkage until said portion has regained sufficient strength to maintain said bones in said standard configuration.

2. The method of claim 1, wherein said ligament is a surgical graft ligament and said thermal shrinkage is applied in a process of stretching said ligament after attachment of said graft ligament to said bones.

3. The method of claim 1, wherein said ligament is a natural ligament.

4. The method of claim 1, wherein said radio frequency energy is applied to said ligament arthroscopically.

5. The method of claim 4, wherein applying said energy arthroscopically comprises providing an insulated probe having an electrode in a distal portion thereof, introducing said probe into a body cavity adjacent said ligament, and applying said energy through said electrode to said ligament.

6. The method of claim 1, wherein energy is applied to said ligament by two electrodes positioned on opposite sides of said ligament.

7. The method of claim 1, wherein said tension is maintained below that necessary to stretch said portion of said ligament by tension-relieving sutures in said ligament.

8. The method of claim 1, wherein said tension is maintained below that necessary to stretch said portion of said ligament by maintaining said bones in a substantially fixed position.

9. The method of claim 1, wherein said method further comprises releasing tension on said ligament being treated by a surgical incision to a ligament not being concurrently treated.

10. A method for treating ligament-induced skeletal shift, comprising:

applying radio frequency energy to a portion of one ligament of a set of ligaments of a patient that function to align two or more bones in a standard configuration in a species to which said patient belongs but which are causing a skeletal shift in said patient because of an imbalance of ligament-induced forces in said patient for a time sufficient to induce thermal shrinkage of said portion of said ligament, thereby alleviating said skeletal shift.

11. The method of claim 10, wherein said skeletal shift is patellar shift and a medial ligament is shortened.

12. The method of claim 10, wherein said skeletal shift is a twisting of the spinal column of said patient and said ligament is attached to two or more vertebrae of said spinal column.

* * * * *

UNITED STATES PATENT AND TRADEMARK OFFICE
CERTIFICATE OF CORRECTION

PATENT NO. : 5,954,716
DATED : September 21, 1999
INVENTOR(S) : Hugh R. Sharkey et al.

It is certified that error appears in the above-identified patent and that said Letters Patent is hereby corrected as shown below:

<u>Title page,</u>
Item [75], Inventors, please add -- Hansen Yuan, Fayetteville, NY --.

Signed and Sealed this

Seventeenth Day of December, 2002

JAMES E. ROGAN
*Director of the United States Patent and Trademark Office*